United States Patent
Brazzell et al.

(12) 
(10) Patent No.: US 6,214,819 B1
(45) Date of Patent: Apr. 10, 2001

(54) METHOD FOR TREATING OCULAR NEOVASCULAR DISEASES

(75) Inventors: Romulus Kimbro Brazzell, Alpharetta, GA (US); Jeanette Marjorie Wood, Biel Benken (CH); Peter Anthony Campochiaro, Baltimore, MD (US); Frances Elizabeth Kane, Gainesville, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/442,781

(22) Filed: Nov. 18, 1999

(51) Int. Cl.⁷ .................................................. A61K 31/395
(52) U.S. Cl. ....................................................... 514/211.08
(58) Field of Search .......................................... 514/211.08

(56) References Cited

U.S. PATENT DOCUMENTS

| | | | |
|---|---|---|---|
| 5,093,330 | 3/1992 | Caravatti et al. | 514/211 |
| 5,919,813 | * 7/1999 | De Juan | 514/432 |
| 5,980,929 | * 11/1999 | De Juan | 514/427 |
| 6,028,099 | * 2/2000 | De Juan | 514/434 |

FOREIGN PATENT DOCUMENTS

WO 97/34920    9/1997  (WO).
WO 97/40831    11/1997 (WO).

OTHER PUBLICATIONS

A derivative of Staurosporine (CGP 41 251) Shows Selectively for Protein Kinase C Inhibition and In Vitro Anti-Proliferative as Well as In-Vivo Anti-Tumor Activity, Thomas Meyer, et al., Int. J. Cancer: 43, 851-859 (1989).

Migration of Retinal Pigment Epithelim Cells in Vitro is Regulated by Protein Kinase C, Todd L. Murphy, et al, Exp. eye Res. (1995) 60, 683-695.

Evolution of Neovascularization in Mice with Overexpression of Vascular Endothelial Growth Factor in Photoreceptors, T. Takao et al, Investigative Ophthalmology & Visual Science, Jan. 1998, vol. 39, No. 1, 180-188.

Analogs of Staurosporine: Potential Anticancer Drugs?, Andreas Gescher, Gen. Pharmac. vol. 31, No. 5, pp. 721-728, 1998.

* cited by examiner

*Primary Examiner*—James H. Reamer
(74) *Attorney, Agent, or Firm*—David E. Wildman; Robert J. Gorman

(57) ABSTRACT

The invention provides a method for treating or preventing ocular neovascularization. The method administers an effective amount of a staurosporine derivative to treat or prevent retinal or choroidal neovascularization. In each case, the effect on the pathologic blood vessels is dramatic and profound with complete or near-complete inhibition, but there is no identifiable toxic effect on mature retinal vessels.

18 Claims, No Drawings

METHOD FOR TREATING OCULAR NEOVASCULAR DISEASES

BACKGROUND OF THE INVENTION

The invention relates to staurosporine derivatives for treating ocular neovascular disease. More specifically, the invention relates to a method for treating ocular neovascular disease, e.g., retinal neovascularization and choroidal neovascularization, with staurosporine derivatives.

The retina of the eye receives its blood supply from two vascular beds, the retinal vessels which supply the inner two thirds of the retina, and the choroidal vessels which supply the outer one third. Damage to retinal blood vessels resulting in closure of retinal capillaries occurs in several disease processes including diabetic retinopathy, retinopathy of prematurity, branch retinal vein occlusion, and central retinal vein occlusion; they are collectively referred to as ischemic retinopathies. Retinal ischemia results in release of one or more angiogenic factors that stimulate neovascularization. The new vessels break through the internal limiting membrane (ILM) that lines the inner surface of the retina and grow along the outer surface of the vitreous. They recruit many other cells and produce sheets of vessels, cells, and extracellular matrix that exert traction on the retina, often leading to retinal detachment and severe loss of vision.

Choroidal neovascularization occurs in a number of disease processes, the most common of which is age-related macular degeneration. In this condition, the macula, which is especially adapted for acute and detailed vision, is damaged by gradual death of photoreceptor and RPE cells. This constitutes the degeneration part of the disease which results in the gradual loss of central vision. The reason for the cell death is unknown and there is currently no treatment. As the degeneration occurs, there is a tendency for new blood vessels to grow from the choroid to invade the sub-RPE and subretinal spaces. This process is called choroidal neovascularization (CNV) and it often leads to rapid and severe loss of vision from bleeding and scarring. If the CNV is well-delineated and not beneath the center of the fovea, which is true for a small minority of patients, laser treatment can sometimes help. Even when laser is initially successful, there is a high rate of recurrent CNV and loss of vision. A treatment directed at the stimuli for blood vessel growth is needed and would benefit patients with either retinal or choroidal neovascularization.

SUMMARY OF THE INVENTION

There is provided in accordance with the present invention a method for treating or preventing ocular neovascular diseases, including retinal neovascularization and choroidal neovascularization. The method has the step of administering an effective amount of a staurosporine derivative or a salt thereof.

The staurosporine treatment of the present invention is highly effective in inhibiting and preventing ocular neovascularization, unlike prior art laser treatment that has a limited efficacy. In addition, the staurosporine treatment is simple to administer, unlike prior art treatment methods, e.g., laser treatment, that are invasive and require complex equipment.

DETAILED DESCRIPTION OF THE INVENTION

The present invention provides a method for treating ocular neovascular diseases. The method uses a medicament containing a staurosporine derivative. It has now surprisingly been found that the compounds of formula (I) are highly useful for treating ocular neovascularization, including retinal neovascularization and choroidal neovascularization.

Suitable staurosporine derivatives for the present invention have the formula (I):

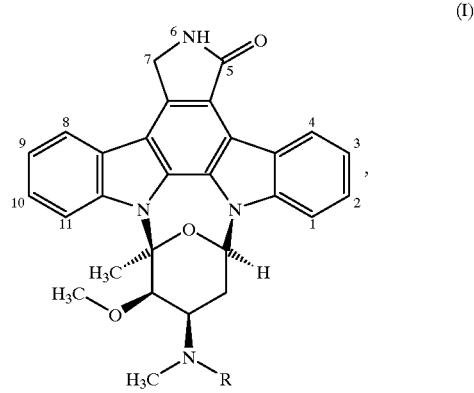

(I)

wherein R represents a hydrocarbyl radical $R^\circ$ or an acyl radical Ac. Suitable hydrocarbyl radicals include acyclic, carbocyclic and carbocyclic-acyclic hydrocarbyl radicals having a maximum total number of carbon atoms of preferably 30, especially 18. Additionally suitable hydrocarbyl radicals are heterocyclic radicals and heterocyclic-acyclic radicals. The hydrocarbyl radicals ($R^\circ$) may be saturated or unsaturated and substituted or unsubstituted. Suitable acyl radicals include optionally functionally modified carboxylic acid and organic sulfonic acid, and optionally esterified phosphoric acid, e.g., pyro- or ortho-phosphoric acid.

Preferred acyclic hydrocarbyl radicals include $C_1$–$C_{20}$-alkyl radicals; $C_2$–$C_{20}$ hydroxyalkyl radicals of which the hydroxy group is in any position other than the 1-position; cyano-[$C_1$–$C_{20}$]-alkyl radicals; carboxy-[$C_1$–$C_{20}$]-alkyl radicals of which the carboxy group; and $C_3$–$C_{20}$-alkenyl radicals of which the free valency is not at the same carbon atom as the double bond. Exemplary acyclic hydrocarbyl radicals are radicals of lower alkyl, e.g., methyl, ethyl, propyl, butyl, pentyl, hexyl and heptyl; lower alkenyl, e.g., propenyl, 2- or 3-methallyl and 2- or 3-butenyl; lower alkadienyl, e.g., 1-penta-2,4-dinyl; and lower alkynyl, e.g., propargyl or 2-butynyl. Preferred carbocyclic hydrocarbyl radicals are radicals of mono-, bi- or polycyclic cycloalkyl, e.g., cyclopropyl, cyclobutyl, cyclopentyl, cyclohexyl, bicyclo[2,2,2]octyl, 2-bycyclo[2,2,1]heptyl and adamantyl; cycloalkenyl; cycloalkandienyl; and corresponding aryl. Aryl radicals include radicals of phenyl, napthyl (e.g., 1- or 2-napthyl), biphenylyl (e.g., 4-biphenylyl), anthryl, fluorenyl, azulenyl, and aromatic analogues thereof having one or more saturated rings. Preferred carbocyclic-acyclic radicals are acyclic radicals that carry one or more of carbocyclic radicals. Heterocyclic radicals and heterocyclic-acyclic radicals include monocyclic, bicyclic, polycyclic, aza-, thia-, oxa-, thaza-, oxaza-, diaza-, triaza-, and tetraza-cyclic radicals of aromatic character.

Exemplary acyl radicals derived from an optionally functionally modified carboxylic acid ($Ac^1$) have the formula Z—C(=W)— in which W is oxygen, sulfur, or imino and Z is hydrogen, hydrocarbyl $R^\circ$, hydrocarbyloxy $R^\circ O$, or amino. Preferably, W is oxygen or sulfur, and Z is $C_1$–$C_7$ alkyl, especially $C_1$–$C_4$ alkyl, which is optionally substituted by halogen, carboxy or $C_1$–$C_4$ alkoxycarbonyl. Additionally preferred Z is phenyl, pyridyl, furyl, thienyl, imidazolyl, quinolyl, isoquinolyl, benzofuranyl or benzimidazolyl, each of which is unsubstituted or substituted by $C_1$–$C_4$ alkyl, $C_1$–$C_4$ alkoxy, halogen, nitro, trifluoromethyl, carboxy, $C_1$–$C_4$ alkoxycarbonyl, methylenedioxy, cyano and/or a salt thereof. Preferred $Ac^1$ acyl radicals have the formula $R_b^o$—CO—, in which $R_b^o$ is hydrogen, benzoyl, or a hydrocarbyl radical, e.g., $C_1$–$C_{19}$ alkyl radical which is optionally substituted by a carboxy group, cyano group, ester group, amino group or helogen. Another group of preferred $Ac^1$ acyl radicals have the formula $R^o$—O—CO—. Yet another group of preferred $Ac^1$ acyl radicals have the formula

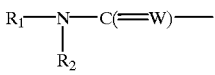

in which $R_1$ and $R_2$ are independently selected from hydrogen and unsubstituted acyclic $C_1$–$C_7$ hydrocarbyl, preferably $C_1$–$C_4$ alkyl and $C_3$–$C_7$ alkenyl. $R_1$ and $R_2$, independently, can be monocyclic aryl, aralkyl or aralkenyl having a maximum of 10 carbon atoms, each of which is optionally substituted by $C_1$–$C_4$ alkyl, $C_1$–$C_4$ alkoxy, halogen and/or nitro. Particularly desirable radicals of this group have hydrogen as $R_1$ and optionally substituted $C_1$–$C_4$ alkyl, $C_3$–$C_7$ alkenyl, phenyl, pyridyl, pyrimidyl, furyl, thienyl, imidazolyl, quinolyl, isoquinolyl, benzofuranyl or benzimidazolyl as $R_2$.

Exemplary acyl radicals derived from an organic sulfonic acid ($Ac^2$) have the formula $R^o$—$SO_2$— in which $R^o$ is a hydrocarbyl radical. Preferably, $R^o$ of the sulfonic acid acyl radicals is $C_1$–$C_7$ alkyl, phenyl, pyridyl, pyrimidyl, furyl, thienyl, imidazolyl, quinolyl, isoquinolyl, benzofuranyl or benzimidazolyl, each of which is unsubstituted or is substituted by $C_1$–$C_4$ alkyl, $C_1$–$C_4$ alkoxy, halogen, nitro, trifluoromethyl, carboxy, $C_1$–$C_4$ alkoxycarbonyl, methylenedioxy, cyano and/or a salt thereof.

Exemplary acyl radicals derived from optionally esterified phosphoric acid ($Ac^3$) have the formula

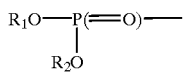

in which $R_1$ and $R_2$ are independently selected from hydrogen, unsubstituted acyclic $C_1$–$C_7$ hydrocarbyl, preferably $C_1$–$C_4$ alkyl and $C_3$–$C_7$ alkenyl. $R_1$ and $R_2$, independently, can be monocyclic aryl, aralkyl or aralkenyl having a maximum of 10 carbon atoms, each of which is optionally substituted by $C_1$–$C_4$ alkyl, $C_1$–$C_4$ alkoxy, halogen and/or nitro.

Additionally suitable staurosporine derivatives include staurosporines of formula (I) in which R is derived from an a-amino acid selected from glycine, phenylglycine, alanine, phenylalanine, proline, leucine, serine, valine, tyrosine, arginine, histidine and asparagine, or a salt thereof. Suitable staurosporine derivatives for the present invention are disclosed in further detail in U.S. Pat. No. 5,093,330 to Caravatti et al. The description of the staurosporine derivatives in the patent is herein incorporated by reference. Particularly preferred staurosporine derivatives of formula (I) for the present invention include: N-(3-carboxypropionyl)-staurosporine, N-benzoyl-staurosporine, N-trifluoracetyl-staurosporine, N-methylaminothiocarbonyl-staurosporine, N-phenylcarbamoyl-staurosporine, N-(3-nitrobenzoyl)-staurosporine, N-(3-fluorobenzoyl)-staurosporine, N-tert-butoxycarbonyl-staurosporine, N-(4-carboxybenzoyl)-staurosporine, N-(3,5-dinitrobenzoyl)-staurosporine, N-alanyl-staurosporine, N-ethyl-staurosporine, N-carboxymethyl-staurosporine, N-[(tert.-butoxycarbonylamino)-acetyl]-staurosporine, N-(2-aminoacetyl)-staurosporine, and pharmaceutically acceptable salts thereof.

The pharmaceutical composition of the present invention which contains a compound of formula I as the active ingredient can be administered enterally, nasally, buccally, rectally, topically, orally, and parenterally, e.g., intravenous, intramuscular, intravitreal, subconjunctival or subcutaneous administration, to treat ocular neovascularization in mammalian subjects, especially human. The compositions may contain the active ingredient alone or, preferably, the active ingredient along with a pharmaceutically acceptable carrier. The effective dosage of the active ingredient depends on the type of targeted disease, as well as the species, age, weight and physical condition of the subject, pharmacokinetic data, and the mode of administration.

The compounds of formula I is administered in an amount effective against pathological conditions of a mammal, e.g., human. For an individual having a bodyweight of about 70 kg, the daily systemic dose administered is from about 0.1 g to about 20 g, preferably from about 0.5 g to about 5 g, of the active ingredient, and suitable pharmaceutical compositions may have from about 1% to about 95% of the active ingredient. Suitable unit dose forms include coated and uncoated tablets, ampoules, vials, suppositories, or capsules. Other suitable dosage forms include injectables, intraocular devices, intravitreal devices, ointments, creams, pastes, foams, tinctures, lip-sticks, eye-drops, oral-drops, sprays, dispersions and the like. The pharmaceutical compositions of the present invention are prepared in a manner known in the art, for example, by means of conventional mixing, granulating, coating, dissolving or lyophilizing processes.

Preference is given to the use of solutions of the active ingredient, and also suspensions or dispersions, especially isotonic aqueous solutions, dispersions or suspensions. Suitable pharmaceutical compositions containing the active ingredient may have carriers, e.g., mannitol and starch, preservatives, stabilizers, wetting agents, emulsifiers, solubilizers, salts for regulating osmotic pressure, buffers and the like. The compositions are prepared in a manner known in the art, for example by means of conventional dissolving and lyophilizing processes. A solution or suspension form of the composition may contain viscosity-increasing agents, e.g., sodium carboxymethylcellulose, carboxymethylcellulose, dextran, polyvinylpyrrolidone, and gelatins; and solubilizers, e.g., Tween 80 [polyoxyethylene (20)sorbitan mono-oleate; trademark of ICI Americas, Inc, USA].

Suitable carriers include fillers, e.g., sugars, for example lactose, saccharose, mannitol or sorbitol; cellulose preparations; calcium phosphates, e.g., tricalcium phosphate and calcium hydrogen phosphate; binders, e.g., starches, methylcellulose, hydroxypropyl methylcellulose, sodium carboxymethylcellulose and polyvinylpyrrolidone; and, if desired, disintegrators, e.g., starches, crosslinked polyvinylpyrrolidone, alginic acid or salts thereof. Additional suitable excipients are flow conditioners and lubricants, e.g., silicic acid, talc, stearic acid and salts thereof, such as magnesium or calcium stearate, polyethylene glycol, and derivatives thereof.

The active ingredient, i.e., a staurosporine derivative, of the present invention completely or substantially completely inhibits ocular neovascularization, especially retinal neovascularization and chorodial neovascularization.

The present invention is further illustrated with the following examples. However, the example is not to be construed as limiting the invention thereto.

EXAMPLES

Example 1

Ischemic retinopathy is produced in C57/BL6J mice by a method described by Smith et al., Oxygen-induced Retinopathy in the Mouse, Invest. Ophthalmol. Vis. Sci. 35, 101–111 (1994). Seven-day-old mice and their mothers are placed in an airtight incubator and exposed to an atmosphere of 75±3% oxygen for 5 days. Incubator temperature is maintained at 23±2° C., and oxygen is measured every 8 hours with an oxygen analyzer. After 5 days, the mice are removed from the incubator, placed in room air, and subjected to a drug treatment. N-benzoyl-staurosporine (NBS) is dissolved in dimethyl sulfoxide (DMSO) and diluted to final concentrations with water; the maximum concentration of DMSO is 1%. Vehicle (1% DMSO) or vehicle containing various concentrations of the drug (volume=10 µl per gram body weight) is placed in the stomach by gavage. Different mice are given 60, 300 or 600 mg of NBS per kg of body weight. As a control, a group of mice are given the vehicle without NBS.

After 5 days of treatment, the mice are sacrificed, eyes are rapidly removed and frozen in optimum cutting temperature embedding compound (OCT; Miles Diagnostics, Elkhart, Ind.) or fixed in 10% phosphate-buffered formalin and embedded in paraffin. Adult C57BL6J mice are also treated by gavage with the drug or vehicle and after 5 days, they are sacrificed and their eyes are processed for frozen or paraffin sections.

Frozen sections (10 µm) of the eyes from drug-treated and control mice are histochemically stained with biotinylated griffonia simplicifolia lectin B4 (Vector Laboratories, Burlingame, Calif.) which selectively binds to endothelial cells. Slides are incubated in methanol/$H_2O_2$ for 10 minutes at 4° C., washed with 0.05 M Tris-buffered saline, pH 7.6 (TBS), and incubated for 30 minutes in 10% normal porcine serum. Slides are incubated 2 hours at room temperature with biotinylated lectin and after rinsing with 0.05M TBS, they are incubated with avidin coupled to peroxidase (Vector Laboratories) for 45 minutes at room temperature. After being washed for 10 minutes with 0.05 M TBS, slides are incubated with diaminobenzidine to give a brown reaction product. Some slides are counterstained with hematoxyln and all were mounted with Cytoseal.

To perform quantitative assessments, 10 µm serial sections are cut through half of each eye and sections roughly 50–60 µm apart are stained with lectin, providing 13 sections per eye for analysis. Lectin-stained sections are examined with an Axioskop microscope (Zeiss, Thornwood, N.Y.) and images are digitized using a 3 CCD color video camera (IK-TU40A, Toshiba, Tokyo, Japan) and a frame grabber. Image-Pro Plus software (Media Cybernetics, Silver Spring, Md.) is used to delineate lectin-stained cells on the surface of the retina and their area is measured. The mean of the 13 measurements from each eye is used as a single experimental value.

The mice with ischemic retinopathy treated with the vehicle without NBS show a marked increase in the area of endothelial cell staining throughout the retina with large clumps of cells on the retinal surface when compared to nonischemic mice, which show normal vessels in the superficial and deep capillary beds with a few connecting vessels. Ischemic mice that are given 600 mg/kg of NBS once a day for 5 days have a dramatic decrease in endothelial cell staining on the surface and within the retina when compared to the vehicle-treated mice. In fact, the endothelial cell staining within the retina of the NBS-treated ischemic mice is less than that of the nonischemic mice. High magnification shows that there are no identifiable endothelial cells on the surface of the retina, indicating that there is complete inhibition of neovascularization. There is also a striking absence of endothelial cell staining in the inner nuclear layer and outer plexiform layer where the deep capillary beds are normally located.

The mice with ischemic retinopathy which are given 300 mg/kg or 60 mg/kg of NBS twice a day by gavage show some clumps of neovascularization on the surface of the retina that is less than clumps in the retina of the vehicle-treated control mice. The retinas of NBS-treated mice also show some decrease in endothelial staining within the retina. The result of the image analysis demonstrated that the endothelial cell staining on and in the retinas of mice treated with 600 or 60 mg/kg once a day, was significantly less than that in vehicle-treated mice and showed a dose-dependent effect when compared to the mice that were treated twice a day. The results clearly demonstrate that the staurosporine derivative inhibits retinal neovascularization.

Example 2

Adult C57BL6J mice are given the vehicle or 600 mg/kg of NBS by gavage once a day and after 5 days, they are sacrificed and their eyes are processed as in Example 1.

Image analysis shows that there is no difference in the total area of endothelial staining in the retina or the appearance of retinal vessels in the NBS-treated mice compared to vehicle-treated mice. The analysis also shows no difference in the amount of retinal endothelial cell staining between the NBS- and vehicle-treated mice. This demonstrates that the staurosporine derivative is not toxic to endothelial cells of mature vessels.

Example 3

Litters of newborn C57/BL6J mice (neonatal mice) are divided into treatment and control groups which received daily subcutaneous injections of 100 mg/kg of the drug or vehicle, respectively. At 7 or 10 days of age, the mice are anesthetized with ether, and perfused with 1 ml of phosphate-buffered saline containing 50 mg/ml of fluorescein-labeled dextran ($2 \times 10^6$ average mw, Sigma, St. Louis, Mo.) as described by Tobe et al., Evolution of Neovascularization in Mice with Overexpression of VEGF in Photoreceptors, Invest. Ophthalmol. Vis. Sci. 39, 180–188 (1998). The eyes are removed and fixed for 1 hour in 10% phosphate-buffered formalin. The cornea and lens are removed and the entire retina is carefully dissected from the eyecup. Radially cuts are made from the edge of the retina to the equator in all 4 quadrants, and the retina is flat-mounted in Aquamount with photoreceptors facing upward. The flat mounts are examined by fluorescence microscopy, and the images are digitized using a 3 CCD color video camera and a frame grabber. Image-Pro™ Plus is used to measure the distance from the center of the optic nerve to the leading front of developing retinal vessels in each quadrant and the mean is used as a single experimental value.

At 7 days of age, retinal vessels in the vehicle-treated mice almost reach the peripheral edge of retina, but in the NBS-treated mice, retinal vessels only extend slightly more than halfway to the periphery. At 10 days of age, the superficial capillary bed is complete and extends all the way to the peripheral edge of the retina, and the deep capillary bed is partially developed. But in the NBS-treated mice, the superficial capillary bed has not yet reached the edge of the retina. The distance from the optic nerve to the vascular front is calculated by image analysis and the differences between the treated and control mice at 7 and 10 days of age is statistically significant. This indicates that the staurosporine derivative inhibits retinal vascular development.

Example 4

C57BL/6J mice are treated in accordance with the Association for Research in Vision and Ophthalmology resolution for the treatment of animals. Choroidal neovascularization is generated by modification of a previously described technique, Tobe et al. Targeted disruption of the FGF2 gene does not prevent choroidal neovascularization in a murine model, Amer. J Path, in press. Briefly, 4 to 5 week old male C57BL/6J mice are anesthetized with ketamine hydrochloride (100 mg/kg body weight) and the pupils are dilated with 1% tropicamide. Three burns of krypton laser photocoagulation (100 μm spot size, 0.1 seconds duration, 150 mW) are delivered to each retina using the slit lamp delivery system of a Coherent Model 920 Photocoagulator and a hand held cover slide as a contact lens. Burns are performed in the 9, 12, and 3 o'clock positions of the posterior pole of the retina. Production of a bubble at the time of laser, which indicates rupture of Bruch's membrane, is an important factor in obtaining CNV, so only mice in which a bubble is produced for all three burns are included. Ten mice are randomly assigned to treatment with vehicle alone, and ten mice are assigned to receive vehicle containing 400 mg/kg/day of NBS given orally by gavage. After 14 days, the mice are killed with an overdose of pentobarbital sodium, and their eyes are rapidly removed and frozen in optimal cutting temperature embedding compound (OCT). Frozen serial sections (10 μm) are cut through the entire extent of each burn and histochemically stained with biotinylated griffonia simplicifolia lectin B4 (Vector Laboratories, Burlingame, Calif.), which selectively binds to endothelial cells. Slides are incubated in methanol/$H_2O_2$ for 30 minutes at 4° C., washed with 0.05 M Tris-buffered saline, pH 7.4 (TBS), and incubated for 30 minutes in 10% normal swine serum. Slides are rinsed with 0.05M TBS and incubated 2 hours at 37° C. with biotinylated lectin. After being rinsed with 0.05M TBS, slides are incubated with Streptavidin-phosphatase (Kirkegaard and Perry Laboratories, Cabin John, Md.) for 30 minutes at room temperature. After a 10 minute incubation in 0.05 M Tris buffer, pH 7.6, slides are developed in Histomark Red (Kirkegaard and Perry) to give a red reaction product, and mounted with Cytoseal (Stephens Scientific, Riverdale, N.J.). Some slides are counterstained with Contrast Blue (Kirkegaard and Perry).

To perform quantitative assessments, lectin-stained sections are examined with an Axioskop microscope (Zeiss, Thornwood, N.Y.) and images are digitized using a 3 CCD color video camera (IK-TU40A, Toshiba, Tokyo, Japan) and a frame grabber. Image-Pro Plus software (Media Cybernetics, Silver Spring, Md.) is used to delineate and measure the area of lectin-stained blood vessels in the subretinal space. For each lesion, area measurements are made for all sections on which some of the lesion appeared and added together to give the integrated area measurement. Values are averaged to give one experimental value per mouse. A 2-sample t-test for unequal variances is performed to compare the log mean integrated area between treatment and control mice.

Two weeks after laser, all lesions in both groups of mice show a discontinuity in Bruch's membrane with roughly equivalent damage to the overlying retina. All mice treated with vehicle alone show large areas of choroidal neovascularization at the site of each laser-induced rupture of Bruch's membrane. There is proliferation of retinal pigmented epithelial cells along the margin of the new vessels. Retinal blood vessels stained with lectin are seen in the overlying retina. In contrast, all mice given 400 mg/kg/day of NBS have very little if any choroidal neovascularization at the site of each laser-induced rupture of Bruch's membrane. In most instances, there is no identifiable lectin-stained neovascular tissue throughout the entire burn, but some burns contained regions in which there are thin discs of lectin-stained tissue. There is mild proliferation of RPE cells. Despite the marked decrease in choroidal neovascularization in the eyes of treated mice, the overlying retinal vessels appear normal. This is best seen in sections with no counterstain.

Quantitation of the integrated area of lectin staining per lesion shows a dramatic decrease in the mice treated with NBS (0.0090182±0.0017540 $mm^2$) compared to lesions in mice treated with vehicle alone (0.0695621±0.0073960 $mm^2$). This difference is highly statistically significant (p=0.004). These results clearly demonstrate that the staurosporine derivative dramatically inhibits chorodial neovascularization.

The above examples illustrate the efficacy of the active ingredient. The staurosporine derivatives of the present invention are highly effective in completely or substantially completely inhibiting retinal and chorodial neovascularization, and the active ingredients can be administered to a patient by a drug treatment mode which is conventional and/or practical.

What is claimed is:

1. A method of treating or preventing ocular neovascular diseases, comprising administering an effective amount of a pharmaceutical composition, wherein said pharmaceutical composition comprises a compound of formula I or a salt thereof, wherein formula I is

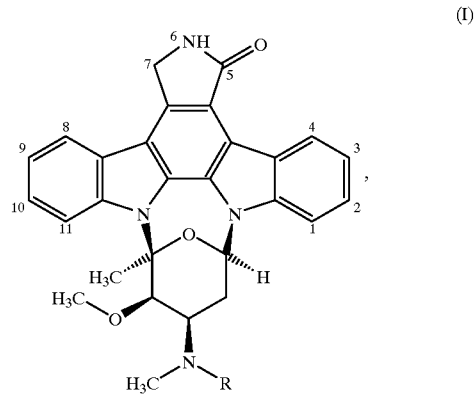

and wherein R is a hydrocarbyl radical or an acyl radical.

2. The method of claim 1 wherein said hydrocarbyl radical is an acyclic, carbocyclic, carbocyclic-acyclic, heterocyclic or heterocyclic-acyclic hydrocarbyl radical.

3. The method of claim 2 wherein said acyclic hydrocarbyl radical is a radical of a $C_1$–$C_{20}$-alkyl radical, $C_2$–$C_{20}$ hydroxyalkyl radical of which the hydroxy group is in any position other than the 1-position, cyano-[$C_1$–$C_{20}$]-alkyl radical, carboxy-[$C_1$–$C_{20}$]-alkyl radical of which the carboxy group, or $C_3$–$C_{20}$-alkenyl radical of which the free valency is not at the same carbon atom as the double bond.

4. The method of claim 2 wherein said carbocyclic hydrocarbyl radical is a radical of mono-, bi- or polycyclic cycloalkyl; cycloalkenyl; cycloalkandienyl; and aryl.

5. The method of claim 2 wherein said carbocyclic-acyclic radicals is an acyclic radical that carry one or more of carbocyclic radicals, and said heterocyclic radical and heterocyclic-acyclic radical are monocyclic, bicyclic, polycyclic, aza-, thia-, oxa-, thaza-, oxaza-, diaza-, triaza-, and tetraza-cyclic radicals of aromatic character.

6. The method of claim 1 wherein said acyl radical is an optionally functionally modified carboxylic acid, organic sulfonic acid, or optionally esterified phosphoric acid.

7. The method of claim 6 wherein said acyl radical has the formula Z—C(=W)—, wherein W is oxygen, sulfur, or imino and Z is hydrogen, $C_1$–$C_7$ alkyl, amino, phenyl, pyridyl, furyl, thienyl, imidazolyl, quinolyl, isoquinolyl, benzofuranyl or benzimidazolyl.

8. The method of claim 6 wherein said acyl radical has the formula $R_b^o$—CO—, wherein $R_b^o$ is hydrogen, benzoyl, or a $C_1$–$C_{19}$ alkyl radical.

9. The method of claim 6 wherein said acyl radical has the formula $R^o$—O—CO—, wherein $R^o$ is an acyclic, carbocyclic, carbocyclic-acyclic, heterocyclic or heterocyclic-acyclic hydrocarbyl radical.

10. The method of claim 6 wherein said acyl radial has the formula

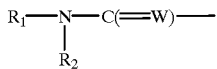

wherein $R_1$ and $R_2$ are independently selected from hydrogen and unsubstituted acyclic $C_1$–$C_7$ hydrocarbyl.

11. The method of claim 6 wherein said acyl radial has the formula $R^o$—$SO_2$— wherein $R^o$ is a hydrocarbyl radical.

12. The method of claim 6 wherein said acyl radical has the formula

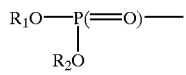

in which $R_1$ and $R_2$ are independently selected from hydrogen, unsubstituted acyclic $C_1$–$C_7$ hydrocarbyl.

13. The method of claim 1 wherein said active ingredient is selected from N-(3-carboxypropionyl)-staurosporine, N-benzoyl-staurosporine, N-trifluoracetyl-staurosporine, N-methylaminothiocarbonyl-staurosporine, N-phenylcarbamoyl-staurosporine, N-(3-nitrobenzoyl)-staurosporine, N-(3-fluorobenzoyl)-staurosporine, N-tert-butoxycarbonyl-staurosporine, N-(4-carboxybenzoyl)-staurosporine, N-(3,5-dinitrobenzoyl)-staurosporine, N-alanyl-staurosporine, N-ethyl-staurosporine, N-carboxymethyl-staurosporine, N-[(tert.-butoxycarbonylamino)-acetyl]-staurosporine, N-(2-aminoacetyl)-staurosporine, and salts thereof.

14. The method of claim 1 wherein said active ingredient is N-benzoyl-staurosporine or a salt thereof.

15. The method of claim 1 is adapted for treating human ocular neovascular diseases.

16. The method of claim 1 is adapted for treating human retinal neovascular diseases.

17. The method of claim 1 is adapted for treating human chorodial neovascular diseases.

18. The method of claim 1 is adapted for treating mammalian ocular neovascular diseases.

* * * * *

UNITED STATES PATENT AND TRADEMARK OFFICE
CERTIFICATE OF CORRECTION

PATENT NO.    : 6,214,819 B1
DATED         : April 10, 2001
INVENTOR(S)   : Brazzell et al.

It is certified that error appears in the above-identified patent and that said Letters Patent is hereby corrected as shown below:

Title page,
Under Item [22], insert:
-- Related U.S. Application Data
[60] Provisional Application Serial No. 60/304,203, converted from Serial No. 09/198,677, abandoned. --

Column 1,
Lines 4-6, -- This application claims the benefit under 35 U.S.C. §119(e) of U.S. Provisional Application No. 60/304,203, filed Nov. 23, 1998, which was converted from U.S. Patent Application No. 09/198,677, and which is incorporated herein by reference. --

Column 2,
Structural formula (I), replace with the following structure:

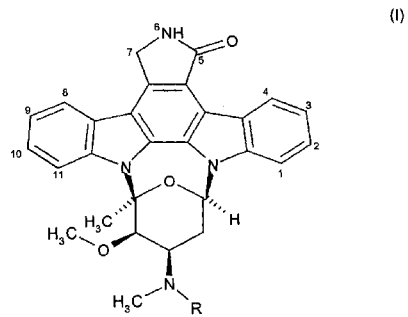

Column 8,
Structural formula (I), replace with the following structure:

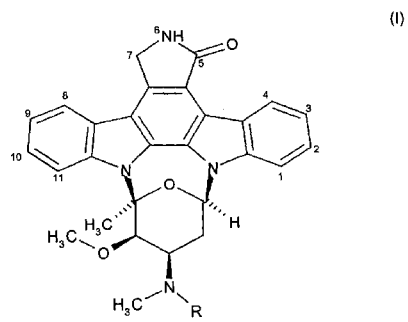

UNITED STATES PATENT AND TRADEMARK OFFICE
CERTIFICATE OF CORRECTION

PATENT NO. : 6,214,819 B1
DATED : April 10, 2001
INVENTOR(S) : Brazzell et al.

It is certified that error appears in the above-identified patent and that said Letters Patent is hereby corrected as shown below:

Column 3,
Line 11, change "acryl" to -- acyl --.
Line 13, change "acryl" to -- acyl --.

Column 9,
Line 24, change "radial" to -- radical --.
Line 34, change "radial" to -- radical --.

Signed and Sealed this

Twenty-fifth Day of June, 2002

Attest:

JAMES E. ROGAN
Attesting Officer   Director of the United States Patent and Trademark Office